(12) United States Patent
Windolf et al.

(10) Patent No.: US 11,376,048 B2
(45) Date of Patent: Jul. 5, 2022

(54) DEVICE FOR CORRECTING UNBALANCED GROWTH PLATE ACTIVITY AND FOR ORTHODONTIC APPLICATIONS

(71) Applicant: AO TECHNOLOGY AG, Chur (CH)

(72) Inventors: Markus Windolf, Davos (CH); Michael Schuetz, St Lucia (AU)

(73) Assignee: AO Technology AG, Chur (CH)

( * ) Notice: Subject to any disclaimer, the term of this patent is extended or adjusted under 35 U.S.C. 154(b) by 174 days.

(21) Appl. No.: 16/339,777

(22) PCT Filed: Oct. 4, 2017

(86) PCT No.: PCT/CH2017/000088
§ 371 (c)(1),
(2) Date: Apr. 5, 2019

(87) PCT Pub. No.: WO2018/064781
PCT Pub. Date: Apr. 12, 2018

(65) Prior Publication Data
US 2020/0038079 A1    Feb. 6, 2020

(30) Foreign Application Priority Data
Oct. 6, 2016   (CH) .................................. 01338/16

(51) Int. Cl.
*A61B 17/82*    (2006.01)
*A61B 17/86*    (2006.01)

(52) U.S. Cl.
CPC .............. *A61B 17/82* (2013.01); *A61B 17/86* (2013.01)

(58) Field of Classification Search
CPC ................................ A61B 17/82; A61B 17/86
See application file for complete search history.

(56) References Cited

U.S. PATENT DOCUMENTS

| | | | | |
|---|---|---|---|---|
| 5,108,433 A | * | 4/1992 | May ...................... | A61F 2/0811 623/13.13 |
| 5,556,428 A | * | 9/1996 | Shah .................. | A61B 17/1146 606/151 |
| 5,575,819 A | * | 11/1996 | Amis ........................ | A61F 2/08 623/13.13 |
| 5,645,423 A | | 7/1997 | Collins, Jr. | |
| 2006/0167459 A1 | | 7/2006 | Groiso | |
| 2010/0198221 A1 | | 8/2010 | Hearn | |
| 2011/0295253 A1 | * | 12/2011 | Bonutti .............. | A61B 17/7059 606/62 |

(Continued)

*Primary Examiner* — Kevin T Truong
*Assistant Examiner* — Tracy L Kamikawa
(74) *Attorney, Agent, or Firm* — Rankin, Hill & Clark LLP

(57) ABSTRACT

An assembly for correcting unbalanced growth plate activity including: (a) an implant formed of wire having (i) a longitudinal central section (2), (ii) a first end (3) configured as a first loop (4) in a form of a first helical coil (9) having a central axis (5) that is transverse to a longitudinal axis of the central section, and (iii) a second end (6) configured as a second loop (7) having a central axis (8) that is transverse to the longitudinal axis of the central section; (b) a first bone screw having a shaft section that is insertable through the first loop; and (c) a second bone screw having a shaft section that is insertable through the second loop. A kit for correcting unbalanced growth plate activity and to a method for correcting unbalanced growth plate activity are also disclosed.

20 Claims, 4 Drawing Sheets

(56) References Cited

U.S. PATENT DOCUMENTS

| | | | |
|---|---|---|---|
| 2012/0209338 A1* | 8/2012 | Groiso | A61B 17/0642 140/71 R |
| 2012/0271358 A1 | 10/2012 | Stevens et al. | |
| 2015/0216565 A1 | 8/2015 | Paley et al. | |

* cited by examiner

DEVICE FOR CORRECTING UNBALANCED GROWTH PLATE ACTIVITY AND FOR ORTHODONTIC APPLICATIONS

PRIORITY CLAIM

This application is a U.S. national stage of International Application No. PCT/CH2017/00008, filed Oct. 4, 2017, and claims priority to Swiss Patent Application No. CH 01338/16, filed Oct. 6, 2016.

BACKGROUND OF INVENTION

Field of Invention

The present invention relates to a device for correcting unbalanced growth plate activity and for orthodontic applications, to an assembly for correcting unbalanced growth plate activity, to a kit for correcting unbalanced growth plate activity and to a method for correcting unbalanced growth plate activity.

Brief Description of Related Art

Pediatric angular limb deformities and length discrepancies are caused by unbalanced growth plate activity. Current clinical practice uses plate and screw constructs spanning the growth plate for single or double sided growth deceleration. These implants are not "passively" safe. They require timely surgical intervention (removal), because ongoing growth leads to steady rise of the reaction force of the fixation, and thereby to plate and screw deformation and consequently to devastating events like implant breakage or growth arrest.

An example of such implants is disclosed in US 2012/0271358.

One problem associated with the above described implant is that the force which it delivers is increasing with the bone growth over time. Therefore these known implants have the inherent danger that the force exerted reaches a critical value which necessitates a surgical intervention in order to prevent breakage of the implant or a growth arrest of the growth plate. Another problem is the so-called "rebound effect", i.e. the deceleration of the growth during the treatment with the implant frequently leads to accelerated growth after removal of the implant, which makes the desired effect void.

What is needed therefore is a device which has the ability of continuously expanding while exerting a constant, displacement independent force to the growth plate over a clearly defined range of displacement.

BRIEF SUMMARY OF THE INVENTION

The invention solves the posed problem with a device for correcting unbalanced growth plate activity and for orthodontic applications as disclosed and claimed herein, with an assembly for correcting unbalanced growth plate activity as disclosed and claimed herein, with a kit for correcting unbalanced growth plate activity as disclosed and claimed herein and with a method for correcting unbalanced growth plate activity as disclosed and claimed herein.

A device is proposed consisting of a wire to be used in an assembly comprising such a device and two bone screws. The two bone screws are inserted proximally and distally to the growth plate.

The device is secured to the protruding shafts of the two bone screws (to the first bone screw by means of the first loop (or helix/coil) and to the second bone screw by means of the second loop (or helix/coil). While the bone grows, the helix of the wire unwinds from the second bone screw exhibiting a, within limits, constant force to the growth plate acting against the direction of growth until the wire has fully unwound and the effect of the implanted device has vanished.

This assembly allows clear steering of the growth deceleration force, mainly determined by the diameter of the wire and the screw shaft diameter over which the helix is positioned, and allows controlling the displacement over which the device should work (determined by the number of windings of the helix). The device according to the invention is passively safe since it will not climax in a catastrophic failure but in gentle detachment of the wire from the second bone screw by means of the unwinding helix.

The implant according to the invention can be attached to the shaft of standard bone screws or specific screws which provide a defined sliding bed for the loops (or helices/coils) of the device and which do not compress the helix between screw and bone.

The advantages of the device according to the invention are essentially the following:
  The device guarantees a constant force independent form the extension of the device (with the devices according to the state of the art the force increases steadily with the growth of the bone).
  Compared to the state of the art devices the device according to the invention is passively safe, i.e. the force cannot reach a critical value which might provoke breakage of the device or a growth arrest of the growth plate; after detachment of the helix from the bone screw the force goes back automatically to 0.
  The maximum possible extension is much larger (10-20 mm) compared to the state of the art; the extension may be predefined be selecting a device with an adequate number of windings of the helix.
  The force to be exerted can be chosen in advance by selecting a device with an appropriate diameter of the wire.
  The device can be used simultaneously on both sides, i.e. medially and laterally (the devices according to the state of the art can be used only on one side), this has the advantage that it is possible to treat angle deformities as well as discrepancies in the length of the leg.

Further advantageous embodiments of the invention can be commented as follows:

Preferably the wire from which the device is made is a cerclage wire having a circular cross-section.

Preferably, at least one of the first and second loops is an open loop having a free end.

The first loop of the device may be a closed loop. The loop may be closed by means of welding, crimping or twisting of the free end of the wire at the first end of the device.

The second loop may be in the form of a helix having a free end, preferably comprising several windings. In an alternative embodiment, the first loop may be in the form of a second helix having a free end, the second helix preferably comprising several windings.

In the case of helices with several windings, the several windings may be arranged parallel to each other with respect to the corresponding central axis or alternatively may be radially stacked on top of each other with respect to the corresponding central axis. This arrangement minimizes the protrusion of the device once it has been implanted in a patient.

In a special embodiment the free end of the wire at the second end of the implant may be rounded-down or blunted. This configuration avoids—after the helix has completely unwound from the second bone screw to which it has been attached—any soft tissue irritations.

Preferably the helix and/or the second helix are cylindrical in shape. Alternatively they may be deformed to have a conical shape.

Purposefully the diameter of the wire is larger than 1.0 mm (preferably larger than 1.3 mm) but smaller than 2.0 mm (preferably smaller than 1.7 mm). Typically the diameter is 1.5 mm.

The wire may preferably be made of a close annealed implant steel.

In special embodiment the wire has a predetermined breaking point which preferably is located at a distance D>0 from the free end of the wire at the first end or the second end of the implant. The value for D preferably is in the range of $1.0\,r\,\pi < D < 2.0\,r\,\pi$ (r being the radius of the loop or helix). This arrangement allows to control exactly the moment of the detachment of the loop or of the helix from the bone screw. Without the breaking point the moment when the wire jumps off the bone screw is more difficult to predict.

In another embodiment the helix extends in the direction of the central axis of the second loop and preferably, the second helix extends in the direction of the central axis of the first loop.

In a further embodiment the wire extends linearly along a longitudinal axis in the central section.

Preferably, the central axis of the first loop and the central axis of the second loop extend essentially orthogonal to the longitudinal axis of the central section.

In another embodiment the longitudinal section 2 is straight.

Preferably the two central axis 5, 8 are essentially parallel to each other.

In another embodiment the first loop 4 and the second loop 6 are essentially lying in a common plane or in parallel planes.

According to a further aspect of the invention, there is provided an assembly for correcting unbalanced growth plate activity. The assembly comprises:
(i) a device according to the invention;
(ii) a first bone screw destined for insertion into the first loop, and
(iii) a second bone screw destined for insertion into the second loop.

The second bone screw has a shaft section with a diameter smaller or equal to the inner diameter of the second loop.

The first bone screw is preferably identical to the second bone screw.

The second bone screw has a smooth, preferably threadless, and preferably cylindrical shaft section for receiving the second loop of the device.

In a special embodiment the shaft section has a larger diameter than the thread of the second bone screw. This configuration limits the insertion depths of the screw and thereby provides a defined space for the second loop of the device.

The second bone screw may comprise a standard bone screw with a sleeve to be slid over the standard bone screw to host the second loop on its outer surface.

The shaft section has purposefully a diameter equal or larger than 2.4 mm (preferably larger than 3.0 mm) but smaller than 5.0 mm (preferably smaller than 4.4 mm).

The helix and/or second helix of the device may be wound counter-clockwise seen in the insertion direction of the first and/or second bone screw. The advantage obtainable by this measure is that the generated moment will tend to turn the bone screw passing though the helix into the bone rather out of the bone.

In a further embodiment the free end of the first may be oriented towards the head of the second bone screw and/or the free end of the second helix of the device may be oriented towards the head of the first bone screw. Alternatively the free end of the helix may be oriented towards the tip of the first second bone screw and/or the free end of the second helix of the device may be oriented towards the tip of the first bone screw.

According to a further aspect of the invention, there is provided a kit for correcting unbalanced growth plate activity comprising two or more devices according to the invention. The distance between the first axis and the second axis of one of the devices of that kit may be in the range of 11.6 mm to 12.4 mm and for another device of that kit may be in the range of 15.5 mm to 16.5 mm According to a further aspect of the invention, there is provided a method for correcting unbalanced growth plate activity. Such a method could comprise the following steps:
(i) positioning a device according to the invention to the bone to be treated bridging the growth plate;
(ii) pre-drilling holes for the first and second bone screws to be used with the device according to the invention through the first loop, respectively through the second loop into the bone; and
(iii) setting the first and second bone screws into the pre-drilled holes.

Preferably the two holes are pre-drilled at a distance larger than the distance between the two central axes of the device, resulting in a pre-stressed condition of the device. The advantage of this measure is that the pre-stressing avoids a delayed force increase at the beginning of the correction of the unbalanced growth plate activity.

In a special embodiment the first and second bone screws are secured in the bone in a torque limiting way. This prevents the blocking of the windings of the helix.

BRIEF DESCRIPTION OF THE DRAWINGS

Several embodiments of the invention will be described in the following by way of example and with reference to the accompanying drawings in which.

DETAILED DESCRIPTION OF THE INVENTION

Figure 1:
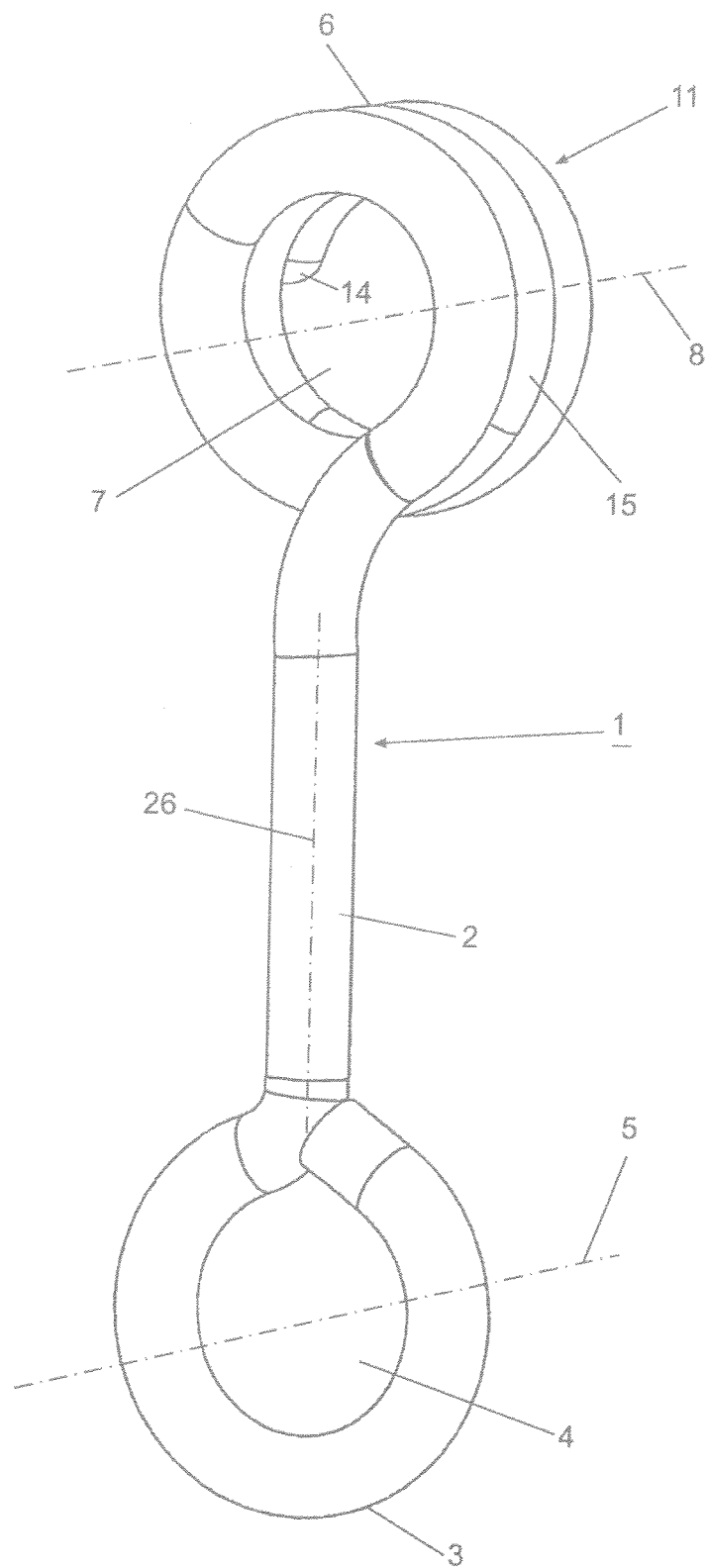
FIG. 1 illustrates a perspective view of an embodiment of the device according to the invention with one helix.

FIG. 1 illustrates an embodiment of the device 1 according to the invention comprising a wire with a longitudinal central section 2, a first end 3 configured as a first loop 4 in form of a closed loop, whose central axis 5 is transverse to the longitudinal central section 2 and a second end 6—whose central axis 8 is transverse to central section 2—configured as a second loop 7 in form of a cylindrical helix 11 comprising several windings 15 arranged parallel to each other with respect to the corresponding central axis 5 and having a free end 14.

The wire is a cerclage wire and has a circular cross-section.

The first loop 4 is closed by means of welding, crimping or twisting of the free end of the wire at the first end 3 of the device 1. The free end of the wire at the second end 6 of the implant 1 is rounded-down.

The diameter of the wire is larger is 1.5 mm and the wire is made of a close annealed implant steel.

The wire extends linearly along a longitudinal axis 26 in the central section 2 and the central axes 5, 8 of the first and second loops 4, 7 extend exemplarily essentially orthogonal to the longitudinal axis 26 of the central section 2. Further, the helix 11 extends in the direction of the central axis 8 of the second loop 7.

Figure 2:
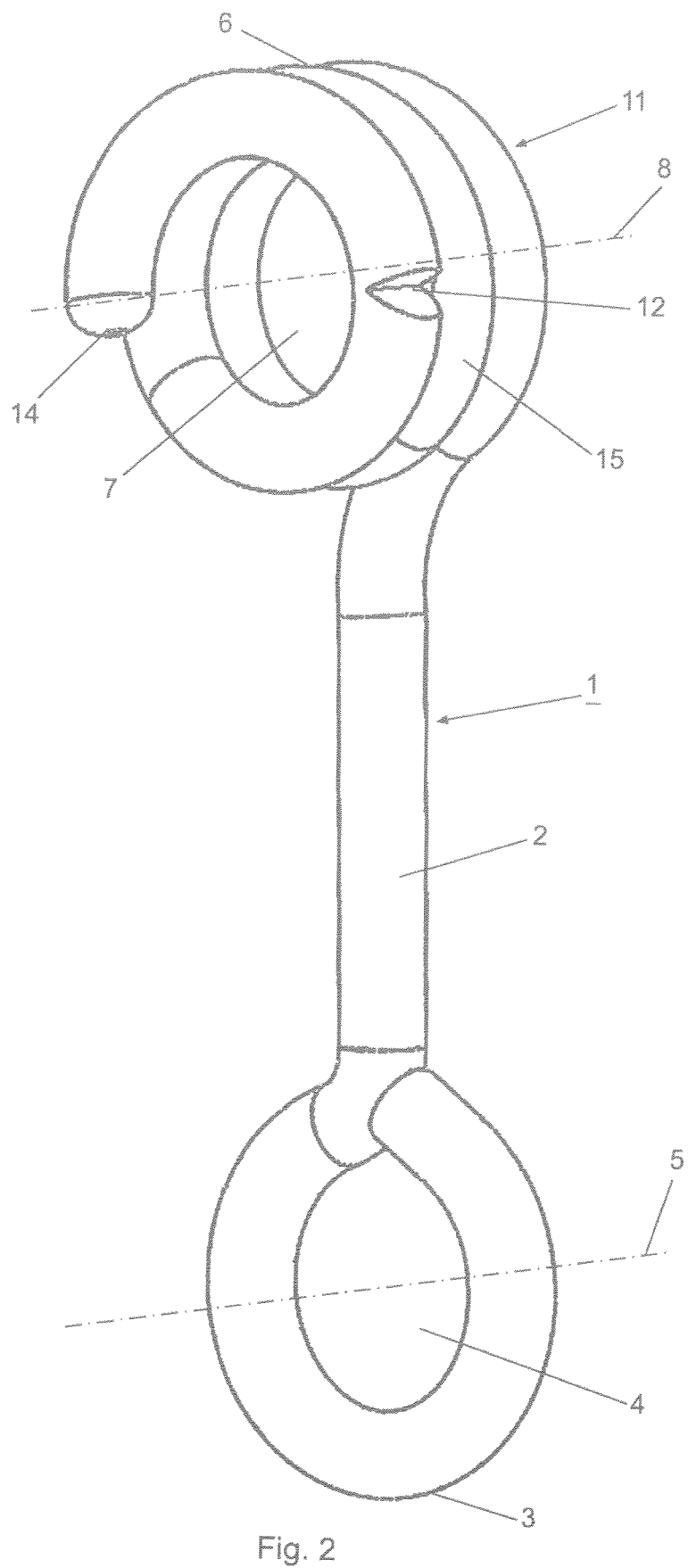
FIG. 2 shows another embodiment of the device according to the invention in perspective view.

FIG. 2 illustrates another embodiment of the device 1 according to the invention similar to that represented in FIG. 1. The difference is to be seen in the different direction of the helix 11 compared to the direction of the helix 11 of the device shown in FIG. 1. As show in FIG. 4 the free end 14 of the helix 11 is oriented towards the head 19 of the second bone screw 17.

Furthermore the wire has a predetermined breaking point 12 which is located at a distance D=1.0 r π from the free end 14 of the wire.

Figure 3:
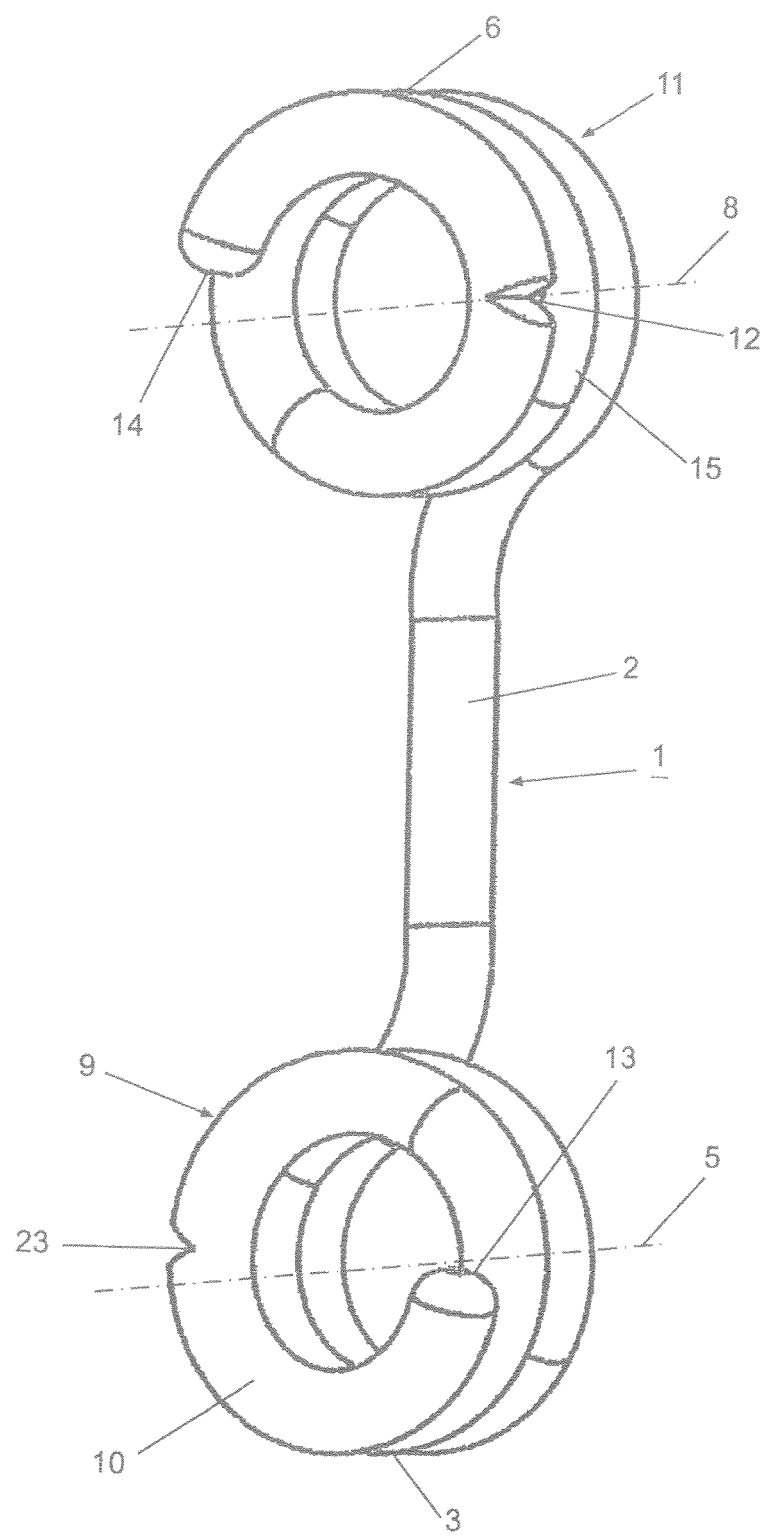
FIG. 3 shows still another embodiment of the device according to the invention with two helices.

FIG. 3 illustrates another embodiment of the device 1 according to the invention with two helices 9, 11 at the first and second end 3,6 of the wire. The second helix 9 has a breaking point 23, a free end 13 and several windings 10, and the helix 11 has a breaking point 12, a free end 14 and several windings 15.

Figure 4:
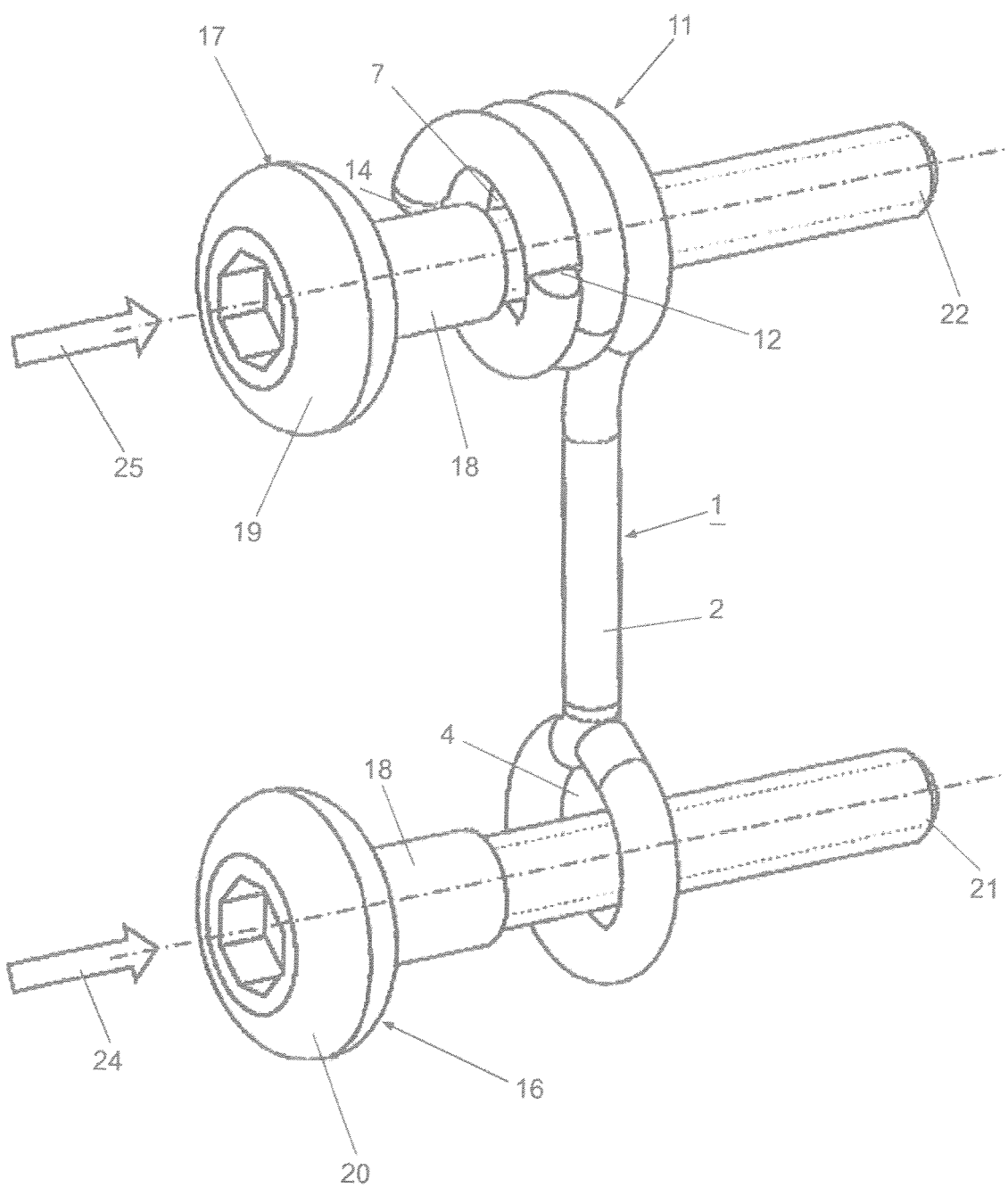
FIG. 4 shows a perspective view of an assembly according to the invention.

FIG. 4 shows an assembly comprising the device shown in FIG. 2 with a first bone screw 16 inserted into the first loop 4 of the device 1 and a second bone screw 17 inserted into the second loop 7 in form of a helix 11.

The second bone screw 17—as well as the first bone screw 16—has a smooth shaft section 18 with a diameter smaller than the inner diameter of the second loop 7. As shown in FIG. 4, each of the first and second bone screws 16, 17 has a head 19, 20, respectively, and a tip 21, 22, respectively.

The arrows 24, 25 indicate the insertion direction in which the bone screws 16, 17 are introduced into the loops 4, 7 and anchored in the bone.

According to the method for correcting unbalanced growth plate activity the following steps are performed: (i) positioning a device 1 according to the invention on the bone to be treated bridging the growth plate; (ii) pre-drilling holes for the first and second bone screws 16, 17 through the first loop 4, respectively through the second loop 7 into the bone; and (iii) setting the first and second bone screws 16, 17 into the pre-drilled holes; and advancing the first and second bone screws 16, 17 into the bone.

Thereby, the two holes are pre-drilled at a distance larger than the distance between the two central axes 5, 8 of the device 1 so that a pre-stressed condition of the device 1 results. The first and second bone screws 16, 17 are preferably secured in the bone in a torque limiting way.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The invention claimed is:

1. An assembly for correcting unbalanced growth plate activity in a bone, comprising:
   a) an implant formed of wire having
      (i) a longitudinal central section,
      (ii) a first end configured as a first loop, said first loop having a central axis that is transverse to a longitudinal axis of the central section, and
      (iii) a second end configured as a second loop being in a form of a helical coil, said helical coil having a central axis that is transverse to the longitudinal axis of the central section;
   b) a first bone screw having a shaft section configured for insertion through the first loop of the implant; and
   c) a second bone screw having a shaft section configured for insertion through the second loop of the implant;
   wherein the second loop is an open loop having a free end, and
   wherein the helical coil is configured to unwind from the shaft section of the second bone screw while applying a controlled force acting against a direction of growth of the growth plate when the implant is attached to the bone with the first and second bone screws such that the longitudinal central section of the implant bridges the growth plate of the bone.

2. The assembly according to claim 1, wherein the first bone screw is identical to the second bone screw.

3. The assembly according to claim 1, wherein the shaft section of the second bone screw is smooth and thread-less.

4. The assembly according to claim 3, wherein the shaft section of the second bone screw has a larger diameter than a thread section of the second bone screw.

5. The assembly according to claim 1, wherein the helical coil is wound counter-clockwise when viewed in an insertion direction of the second bone screw.

6. The assembly according to claim 1, wherein the first loop is a closed loop.

7. The assembly according to claim 6, wherein the closed loop is closed by welding, crimping or twisting the wire at the first end of the implant.

8. The assembly according to claim 1, wherein the helical coil comprises several windings.

9. The assembly according to claim 1, wherein the first loop is in a form of a second helical coil having a free end.

10. The assembly according to claim 1, wherein the helical coil is cylindrical.

11. The assembly according to claim 1, wherein the wire has a predetermined breaking point.

12. The assembly according to claim 1, wherein the central axis of the first loop and the central axis of the second loop extend orthogonal to the longitudinal axis of the central section.

13. The assembly according to claim 1, wherein the longitudinal central section is straight.

14. A kit comprising two or more assemblies according to claim 1.

15. The kit according to claim 14, wherein a distance between the central axis of the first loop and the central axis of the second loop of one of the implants of the two or more assemblies in the kit is in a range of 11.6 mm to 12.4 mm, and a distance between the central axis of the first loop and the central axis of the second loop of a second one of the implants of the two or more assemblies in the kit is in a range of 15.5 mm to 16.5 mm.

16. The assembly according to claim 1, wherein the free end of the second loop is rounded-down or blunted.

17. The assembly according to claim 1, wherein the wire is made of steel and has a diameter larger than 1.0 mm and smaller than 2.0 mm.

18. A method for correcting unbalanced growth plate activity, the method comprising:
   (i) positioning an implant formed of wire of an assembly according to claim 1 on a bone to be treated such that the implant bridges the growth plate;
   (ii) pre-drilling holes for the first and second bone screws through the first loop and the second loop, respectively, into the bone; and
   (iii) setting the first and second bone screws into the pre-drilled holes.

19. The method according to claim 18, wherein the two holes are pre-drilled at a distance larger than a distance between the central axes of the first and second loops of the implant made of wire thereby resulting in a pre-stressed condition of the assembly after setting of the first and second bone screws into the pre-drilled holes.

20. The method according to claim 18, wherein the first and second bone screws are secured in the bone in a torque limiting way.

\* \* \* \* \*